(12) United States Patent
Volker

(10) Patent No.: US 10,271,982 B2
(45) Date of Patent: Apr. 30, 2019

(54) LEG BRACE

(71) Applicant: Monica Ann Volker, Lake Geneva, WI (US)

(72) Inventor: Monica Ann Volker, Lake Geneva, WI (US)

( * ) Notice: Subject to any disclaimer, the term of this patent is extended or adjusted under 35 U.S.C. 154(b) by 497 days.

(21) Appl. No.: 14/061,414

(22) Filed: Oct. 23, 2013

(65) Prior Publication Data

US 2014/0114222 A1    Apr. 24, 2014

Related U.S. Application Data

(60) Provisional application No. 61/717,454, filed on Oct. 23, 2012.

(51) Int. Cl.
*A61F 5/01*    (2006.01)

(52) U.S. Cl.
CPC .......... *A61F 5/0123* (2013.01); *A61F 5/0102* (2013.01); *A61F 5/0127* (2013.01)

(58) Field of Classification Search
CPC .. A61F 5/00; A61F 5/01; A61F 5/0102; A61F 5/0123; A61F 5/0127

USPC .......... 602/16, 23, 26, 27; 128/882
See application file for complete search history.

(56) References Cited

U.S. PATENT DOCUMENTS

| | | | | |
|---|---|---|---|---|
| 5,121,742 | A * | 6/1992 | Engen | 602/16 |
| 5,626,557 | A * | 5/1997 | Mann | A61F 5/012 |
| | | | | 602/13 |
| 6,010,474 | A * | 1/2000 | Wycoki | 602/23 |
| 7,892,195 | B2 * | 2/2011 | Grim | A61F 5/0585 |
| | | | | 128/846 |
| 7,931,567 | B2 * | 4/2011 | Rosenberg et al. | 482/57 |
| 8,021,316 | B2 * | 9/2011 | Franke et al. | 602/23 |
| 2011/0004134 | A1 * | 1/2011 | Barrera | 602/16 |
| 2011/0105969 | A1 * | 5/2011 | Nace | 602/16 |
| 2014/0046234 | A1 * | 2/2014 | DeSousa | 602/16 |

* cited by examiner

*Primary Examiner* — Keri J Nelson
(74) *Attorney, Agent, or Firm* — Casimir Jones, S.C.; David Casimir

(57) ABSTRACT

Provided herein are devices and methods for bracing a leg (e.g., knee braces). Leg braces are provided that immobilize or partially immobilize the knee joint or other portions of the leg, while further providing components for relieving stress associated with body weight of the subject.

8 Claims, 1 Drawing Sheet

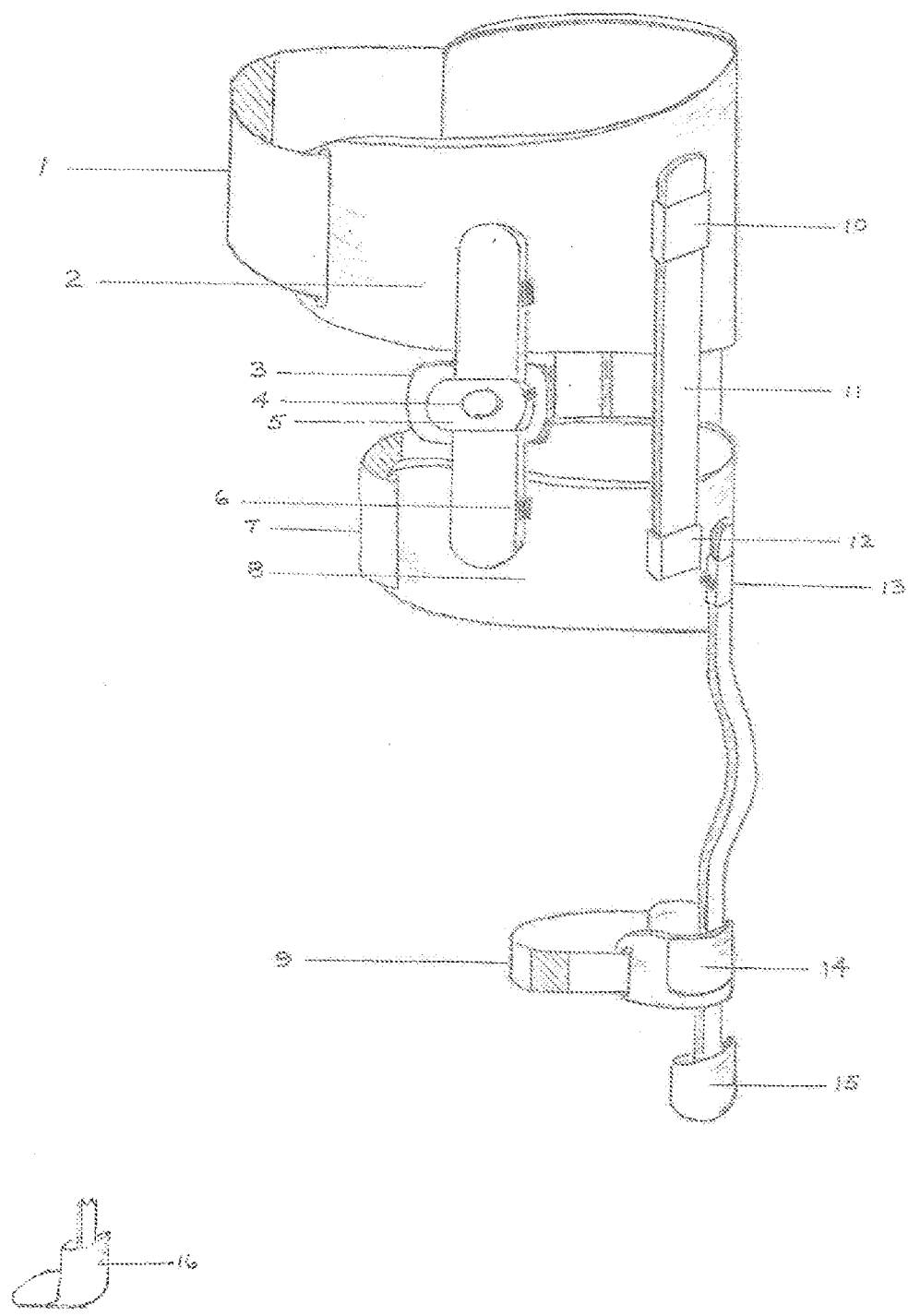

LEG BRACE

This application claims priority to U.S. Provisional Application No. 61/717,454 filed Oct. 23, 2012, which is herein incorporated by reference in its entirety.

FIELD

Provided herein are devices and methods for bracing a leg (e.g., knee braces). Leg braces are provided that immobilize or partially immobilize the knee joint or other portions of the leg, while further providing components for relieving stress associated with body weight of the subject.

BACKGROUND

A knee orthosis (knee brace) is a brace worn to strengthen the knee. Knee braces typically are worn around the knee and work by relieving pressure off the part of the knee joint that is affected by ailments (e.g., arthritis, osteoarthritis, etc.) or that is under recovery from injury (e.g., functional braces) or surgery (e.g., rehabilitation braces). Knee braces are also used to provide stability needed to perform physical activities, whether they are regular daily activities or athletic activities (e.g., prophylactic braces). Knee braces are also used to properly align the knee to help reduce pain (e.g., unloader braces). Not all braces function ideally for all patients or subjects.

BRIEF DESCRIPTION OF THE DRAWINGS

FIG. 1 shows an exemplary leg brace of embodiments of the present disclosure.

DESCRIPTION

Provided herein are devices and methods for bracing a leg (e.g., knee braces). Leg braces are provided that immobilize or partially immobilize the knee joint, while further providing components for relieving stress associated with body weight of the subject.

In some embodiments, the leg brace comprises one or more components that facilitate use with patients of different sizes, including large or heavy patients. These components include, but are not limited to: a) adjustable straps that accommodate any leg size; b) support structures for adding addition physical strength to the device to accommodate heavier body weights without wear, damage, or failure; and c) a component that extends to the ground such that, in operation, the end of the component makes contact with the ground (directly or indirectly) and relieves pressure from a body portion of the subject (e.g., leg, knee, foot, ankle, etc.) that is a component of the subject's body weight. In some embodiments, these components are adjustably extendable so as to allow a "one-size-fits-all" capability for subjects of different heights and leg lengths and sizes. Such devices are particularly beneficial to subjects of high body weight (e.g., obese or overweight subjects). Also provided herein a devices for aligning portions of the leg or foot for subjects in need thereof (e.g., subjects recovering from stroke, amputees, etc.).

An exemplary device is shown in FIG. 1. This device has an upper portion 2 that is configured to attach to a subject's leg above the knee, for example, to a lower thigh region. The upper portion optionally has an adjustable strap 1 that permits the upper portion to fit to any size leg. The adjustable strap may be made of any desired material (e.g., plastic, fabric, leather, etc.). The upper portion is placed on the front of a subject's leg and the strap is adjusted to form a tight fit to the thigh and locked into place using any suitable mechanism (e.g., a buckle, a metal fastener, VELCRO, etc.). The material used for the upper portion may be any suitable material, such as plastic, metal, ceramic, carbon fiber, etc. The upper portion may further comprise one or more pads that make contact with the thigh of the subject. The pad(s) may be removably attached to the inner surface of the upper portion (e.g., via VELCRO, snaps, hooks, etc.).

The device further comprises a lower potion 8 that is configured to attach to a subject's leg below the knee, for example, to an upper calf region. The lower portion may comprise an adjustable strap 7. Other than position and size, the lower portion can be configured similarly to the upper portion 2 in terms of material choices, padding, and the like.

The upper portion 2 and lower portion 8 are connected by a bracing mechanism that relieves pressure from the knee joint and/or properly orients the knee. In some embodiments, this mechanism comprises a torque controlled hinge 4 and a locking component 5 for locking the hinge into a particular location or locations or for otherwise regulating the movement of the hinge (e.g., increasing resistance on a knee bend or flex, allowing flex or bend of the knee, but only through a defined range, providing a plurality of predefined extension positions, etc.). Any desired hinge and locking component can be used (see e.g., U.S. Pat. Nos. 8,062,242, 7,485,103, 7,306,572, 7,201,728, 6,402,711, 5,807,294, 5,632,725, 5,286,250, 5,078,127, 5,074,290, 5,063,916, 4,489,718, and 4,088,130, each of which is herein incorporated by reference in its entirety). In some embodiments, a pad 3 is provided between the hinge on the knee. The pad may be removably attachable to the backside of the locking component 5. In some embodiments, two hinges 4 and locking components 5 are provided on the devices, positioned such that one is located on each side of the knee. Each hinge 4 and locking component 5 operated independent of the other (i.e., each can be adjusted and locked in a different position than the other). Independent operation permits the device to precisely position the knee as desired (e.g., to accommodate healing of ligament damage). In some embodiments, each hinge 4 and locking component 5 are operated dependently to each other (i.e., the positioning or locking of one controls the positioning and locking of the other).

In some embodiments, a bar 6 is provided that attaches to each of the upper portion 2 and the lower portion 8, connecting the two portions. The bar may be made of metal, plastic, ceramic, carbon fiber, or any other desired material. In some embodiments, the bar 6 is adjustable in length to allow any desired positioning of the upper portion 2 and lower portion 8 relative to each other, the knee, or the contact portions on the leg (e.g., to avoid contact with sores, sutures, or other undesired contact points). The proximal and distal ends of the bar 6 are attached (removably or irremovably) to the respective upper and lower portion by any desired mechanism: hook, snap, weld, latch, locking screw, etc.

The device may further comprise one or more immobilization bars 11 that attach to the upper portion 2 and lower portion 8. These immobilization bars assist in controlling the movement of the knee joint and may add additional physical strength to the device to allow the device to relieve more pressure from the knee joint and/or to strengthen the device. The immobilizations bars 11 are made of any desired material (e.g., metal, plastic, ceramic, carbon fiber), and are preferably strong and inflexible. The bars may be of fixed size or may be of adjustable length. The proximal and distal ends of the immobilization bars 11 are attached (preferably removably) to the respective upper and lower portion by any desired mechanism: hook, snap, weld, latch, locking screw, etc. In some embodiments, slot receptacles 10 and 12 are located on the upper and lower portions and configured to receive and position the ends of the immobilization bar 11. In some embodiments two immobilization bars 11 are employed on opposite sides of the device or at any desired angular distance from one another around the circumferences of the device (e.g., 45°, 60°, 90°, 125°, 180°).

In some embodiments, the device further comprises an ankle component 14 to provide further security to the leg and further physical support (e.g., stability and pressure reduction). The ankle components is sized and positioned to attach to the lower portion of the leg near the ankle. The lower portion may comprise an adjustable strap 9. Other than position and size, the ankle component can be configured similarly to the upper portion 2 in terms of material choices, padding, and the like. The ankle component 14 is connected to the lower portion 8 by a bar 13. The bar 13, is preferably adjustable in length, with a locking mechanism to lock the desired length. The proximal and distal ends of the bar 13 are attached (preferably removably) to the respective lower portion 8 and ankle component 14 by any desired mechanism: hook, snap, weld, latch, locking screw, etc. In some embodiments, the bar 13 is shaped to optimize load bearing ability and to conform to the size and shape of the leg of the subject.

In some embodiments, the device comprises a ground support component 15 that contacts the ground, relieving body weight pressure from the knee and leg (or other body parts). In some embodiments, the ground support component resides on the end of bar 13, and is positioned and shaped such that it aligns to the foot or footwear of a subject (e.g., the heel). In some embodiments, the ground support component is positioned behind the foot and is inserted into a shoe behind the heel. The ground support component 15 can be any desired shape and may make contact with the ground (directly or through contact with the inside of shoe or boot, for example) with any shape. For example, the bottom surface of the ground support component 15 can be rounded or flat and may comprise more than one separate contact point (e.g., tripod shaped) with the ground. The ground support component 15 may terminate in a flat panel 16 that runs parallel to the ground (e.g., under the foot, parallel to the plane of gravity). In some embodiments, the ground support component is integrated into or is itself footwear. In some embodiments, the ground support components is shaped and positioned to minimize the risk of tripping or catching on object while the subject is moving.

Also provided herein are methods of using knee braces. A knee brace, as described above, is attached to a subject to regulate the position or bend of the knee and/or to position or align any part of the leg, including the feet. The straps, if present, are adjusted to conform to the leg size of the subject. The lengths of components 6, 11, and 13, if present, are adjusted to appropriate lengths. The ground support component 15, if present, is adjusted to make contact with the ground. Subjects include, but are not limited to, patients with arthritis, osteoarthritis, rehabilitation needs (e.g., from injury or surgery), athletic needs, knee alignment needs, gait management needs, etc.

Further provided herein are kits comprising one or more components of the devices described herein. For example, in some embodiments, a kit comprises all of the components needed to assemble a functional device. In some embodiments, the kit provides alternatively sized individual components to allow mix-and-match size selection of the components to a particular patient.

In some embodiments, a subject utilized a device, as described above, on each of their legs (e.g., two such devices). The device associated with each leg may be the same or may be independently designed and configured for the particular needs of the respective legs. In some embodiments, the two devices are connected to one another to control the position of each relative to the other. Such embodiments find use, for example, to control tremors or provide substantial leg positioning or stability for patients in need thereof (e.g., patients at the early stages of rehabilitation).

In some embodiments, the devices are employed by subjects that have undergone partial leg amputation and or those that employ foot or leg prosthetics. In some such embodiments, a prosthetic may be integrated into the device. For example, a lower leg prosthetic may be connected to the device and serve as the ground support component 15.

I claim:

1. A knee brace comprising:
    a) an upper portion that is configured to attach to a subject's leg above a knee, said upper portion comprising an adjustable strap;
    b) a lower portion that is configured to attach to said subject's leg below the knee, said lower portion comprising an adjustable strap;
    c) an ankle component sized and positioned to attach to said subject's leg near an ankle, wherein said ankle component is connected to said lower portion by an adjustable length bar with locking mechanism;
    d) a ground support component configured to make contact with the ground and to fit within said subject's footwear;
    e) a first immobilization bar having a top end and a bottom end, wherein said top end of said first immobilization bar connects to said upper portion and said bottom end of said first immobilization bar connects to said lower portion; and
    f) a second immobilization bar having a top end and a bottom end, wherein said top end of said second immobilization bar connects to said upper portion opposite to said first immobilization bar and said bottom end of said second immobilization bar connects to said lower portion opposite to said first immobilization bar;
    wherein said upper portion and lower portion are connected by a bracing mechanism comprising a torque controlled hinge and locking component.

2. The knee brace of claim 1, wherein said ankle component comprises an adjustable strap.

3. The knee brace of claim 1, wherein said ground support component terminates in a flat panel that runs parallel to the plane of gravity.

4. The knee brace of claim 3, wherein said ground support component is shaped such that it aligns to the heel of said subject.

5. A method of securing a knee, comprising, attaching the knee brace of claim 1 to a subject.

6. The method of claim 5, wherein the subject is selected from the group consisting of: an obese subject, a subject recovering from injury or surgery, a subject recovering from stroke, and an athlete.

7. A kit comprising components sufficient to assemble the knee brace of claim 1.

8. The knee brace of claim 1, wherein said first and second immobilization bars are removably attached to said upper portion and lower portion by slot receptacles.

\* \* \* \* \*